United States Patent
Sugimoto et al.

(10) Patent No.: US 6,937,269 B2
(45) Date of Patent: *Aug. 30, 2005

(54) ELECTRONIC ENDOSCOPE SELECTOR AND ELECTRONIC ENDOSCOPE SYSTEM

(75) Inventors: Hideo Sugimoto, Tokyo (JP); Makoto Koike, Tokyo (JP)

(73) Assignee: PENTAX Corporation, Tokyo (JP)

( * ) Notice: Subject to any disclaimer, the term of this patent is extended or adjusted under 35 U.S.C. 154(b) by 695 days.

This patent is subject to a terminal disclaimer.

(21) Appl. No.: 09/752,741

(22) Filed: Jan. 3, 2001

(65) Prior Publication Data

US 2001/0007468 A1 Jul. 12, 2001

(30) Foreign Application Priority Data

Jan. 11, 2000 (JP) .................................... P2000-002641

(51) Int. Cl.⁷ ............................................. H04N 9/47
(52) U.S. Cl. ...................................................... 348/74
(58) Field of Search ............................ 348/65, 66, 74, 348/72, 71, 77, 153, 159, 600, 76, 45, 47, 48, 52, 60

(56) References Cited

U.S. PATENT DOCUMENTS 5,243,416 A * 9/1993 Nakazawa ................... 348/74
5,291,276 A * 3/1994 Matsumoto et al. ......... 348/708
5,605,531 A * 2/1997 Lane et al. ................. 600/118
5,877,802 A * 3/1999 Takahashi et al. ............ 348/71
5,995,140 A * 11/1999 Cooper et al. .............. 348/159
6,120,435 A * 9/2000 Eino ........................... 600/118
6,656,949 B1 12/2003 Chen
6,677,984 B2 1/2004 Kobayashi
6,717,609 B2 * 4/2004 Sugimoto et al. ............. 348/74

* cited by examiner

*Primary Examiner*—Chris Kelley
*Assistant Examiner*—Behrooz Senfi
(74) *Attorney, Agent, or Firm*—Greenblum & Bernstein, P.L.C.

(57) ABSTRACT

An electronic endoscope selector that is used in an electronic endoscope system which shares peripheral devices, such as a TV monitor, VCR etc., among a plurality of electronic endoscopes. The electronic endoscope selector comprises switching circuits for switching and selecting video signals and synchronization signals fed from one of the plurality of electronic endoscopes. The selector also comprises amplifiers, gamma correction circuits, a system control circuit and memory. The amplifiers and gamma correction circuits are for adjusting gains and gamma correction of RGB video signals fed from the selected electronic endoscope. Parameters for appropriate gains and gamma correction corresponding to each endoscope are stored in the memory. The system control circuit controls the amplifiers and gamma correction circuits in accordance with the parameters that correspond to the selected electronic endoscope.

5 Claims, 3 Drawing Sheets

ELECTRONIC ENDOSCOPE SELECTOR AND ELECTRONIC ENDOSCOPE SYSTEM

BACKGROUND OF THE INVENTION

1. Field of the Invention

The present invention relates to an electronic endoscope system, which comprises a plurality of electronic endoscope units and peripheral devices, such as TV monitors or VCR's (video cassette recorder).

2. Description of the Related Art

As to its purpose and faculty, various types of electronic endoscope systems are manufactured and sold by various makers. For example, a narrow bronchoscope, which is mainly utilized for observation and diagnosis, an endoscope for a digestive track, which is thick and includes a channel for surgical treatment, such as forceps, etc. There are also types of endoscopes with an elongated insertion portion which is hard/soft, long/short and so on.

An operator may utilize several types of electronic endoscope systems during a single checkup or medical examination, since each type of electronic endoscope system has an exclusive purpose. In electronic endoscopy, captured images are displayed by an image indicating device, such as TV monitor and so on. However, when a plurality of electronic endoscope systems are used simultaneously, it is a dissipation of space and cost to provide TV monitors, video cassette recorders and other peripheral devices for each electronic endoscope system. It is also cumbersome and time consuming to operate the peripheral devices individually prepared for each system.

SUMMARY OF THE INVENTION

Therefore, it is preferable to share devices that can have a common function among the electronic endoscope systems, such as a TV monitor, video cassette recorder (VCR) etc., and build a single organized electronic endoscope system. In order to share the peripheral devices among the plurality of electronic endoscope systems and build an organized electronic endoscope system, an electronic endoscope selector is required to mediate between each of the electronic endoscopes and peripheral devices.

The above organized electronic endoscope system comprises a plurality of electronic endoscope units, each of which comprises an endoscope with an elongated part for insertion into a body cavity or hollow organ, and an image-signal processing unit that processes image signals fed from an imaging device mounted on the distal end of the elongated part of the endoscope.

However, in the above system, the color tones of the images, captured by each electronic endoscope unit, may be dissimilar to each other when displayed on the TV monitor. Therefore, when the color of a diseased part is an essential factor for a diagnosis, an operator may be confused by the above color tone difference and may have difficulty in deciding the correct diagnosis and treatment, as the operator may not know which image of the electronic endoscope unit should be referred to as the criteria for diagnosis. In order to display the images from each electronic endoscope on the TV monitor in the same color tones, the same image should be taken by respective electronic endoscope units, and gains and gamma coefficients in each electronic endoscope units are then adjusted so that each image's color tones displayed on the TV monitor become the same. The above adjustment for each unit may be carried out by operating respective control panels for each unit, thus it is cumbersome and time consuming.

Therefore, an object of the present invention is to provide an electronic endoscope selector that enables a plurality of electronic endoscope units to share a peripheral device and integrate a plurality of electronic endoscope systems into a single organized electronic endoscope system. Further, the object of the present invention is to provide the electronic endoscope selector, which easily adjusts video signals, so that the color tone of images on the image indicating device appear the same for each electronic endoscope unit.

According to the present invention, an electronic endoscope selector is provided that comprises a video signal switching processor, a video-signal processor, an image-state parameter storing processor and an image-state parameter setting processor.

A video signal switching processor selects one electronic endoscope unit among a plurality of electronic endoscope units and feeds video signals obtained by the selected electronic endoscope unit to an image indicating device. The selected electronic endoscope is also switch able to another. The video-signal processor processes the video signals, which are fed to the image indicating device, to adjust a color tone of an image displayed on the image indicating device. The image-state parameter storing processor stores image-state parameters. The image-state parameters are for adjusting the color tone corresponding to each of the electronic endoscope units. The image-state parameter setting processor is used to set the image-state parameters.

Preferably, in the video-signal processor, the color tone is carried out by adjusting gains and gamma factors of the video signals. In this case, the above image-state parameters correspond to the above gains and gamma factors. For example, the video signals are comprised of red, green and blue component video signals and the gains are relatively adjusted to each of the red, green and blue video signals.

Further preferably, the video-signal processor starts to process new selected video signals, in accordance with the image-sate parameters which correspond to the newly selected electronic endoscope unit, just after a selected electronic endoscope unit is switched.

Furthermore, according to the present invention, an electronic endoscope system is provided that comprises a plurality of electronic endoscope units, an image indicating device and an electronic endoscope selector.

The electronic endoscope selector comprises a video signal switching processor, an video-signal processor, an image-state parameter storing processor and an image-state parameter setting processor.

The video signal switching processor selects one electronic endoscope unit among a plurality of electronic endoscope units and feeds video signals obtained by the selected electronic endoscope unit to the image indicating device. Further, the video signal switching processor can switch the selected electronic endoscope unit to another electronic endoscope unit. The video-signal processor processes the video signals, which are then fed to the image indicating device, to adjust the color tone of an image displayed on the image indicating device. The image-state parameter storing processor stores image-state parameters which are used to adjust the color tone of the images corresponding to each of a plurality of electronic endoscope units. The image-state parameter setting processor is used to set the image-state parameters.

BRIEF DESCRIPTION OF THE DRAWINGS

The objects and advantages of the present invention will be better understood from the following description, with reference to the accompanying drawings in which.

DESCRIPTION OF THE PREFERRED EMBODIMENTS

Figure 1:
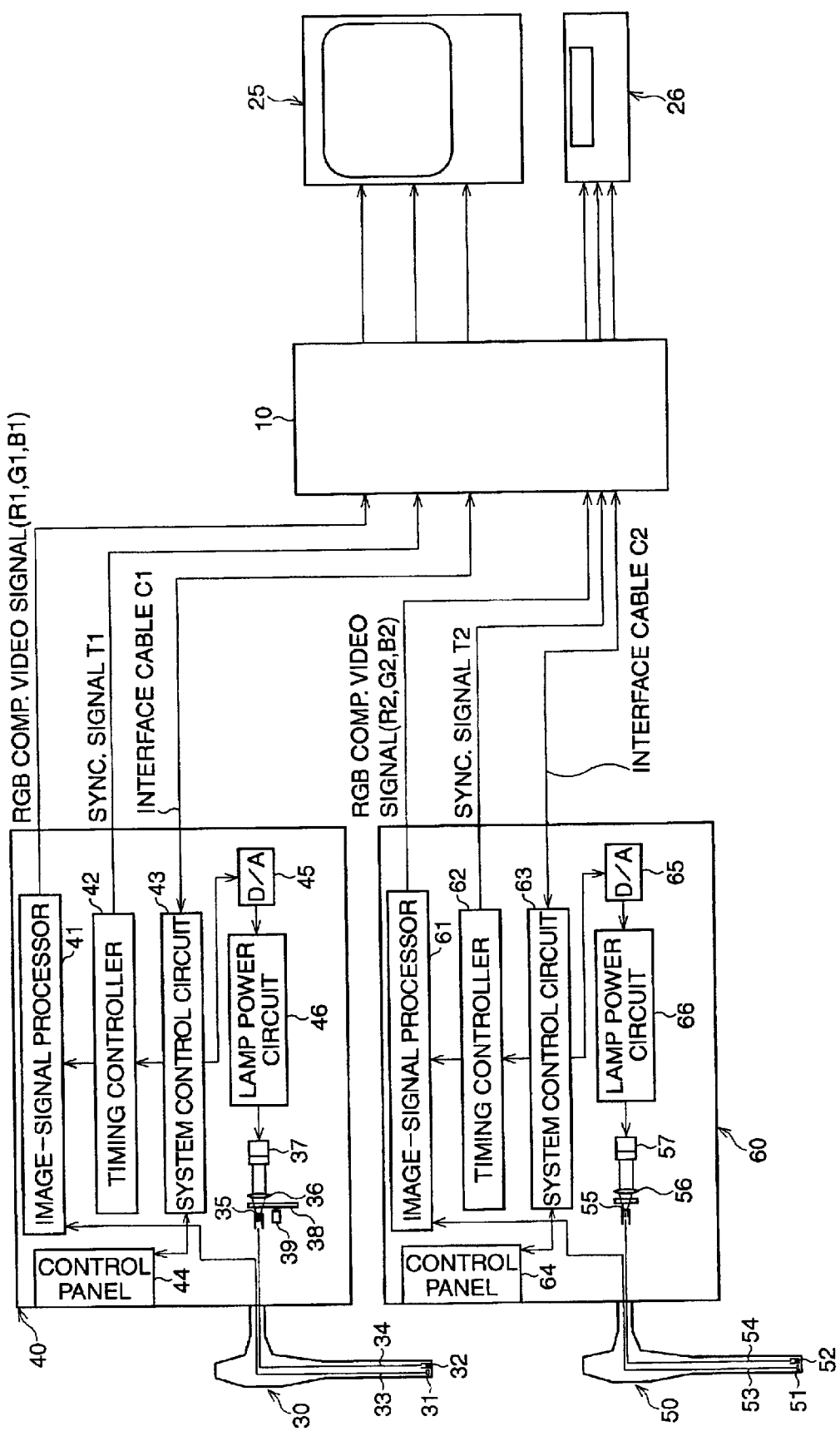
FIG. 1 is a schematic showing an electrical construction of an electronic endoscope system that is integrated with an electronic endoscope selector of the present embodiment of the present invention.

The present invention is described below with reference to the embodiments shown in the drawings.

FIG. 1 is a schematic showing the electrical construction of an electronic endoscope system of the present embodiment and two types of conventional electronic endoscopes utilized in the system.

The image-signal processing units 40 for a RGB sequential method, the image-signal processing units 60 for a color chip method, the TV monitor 25 and VCR 26, which are shared by the above two processing units, are detachably connected to the electronic endoscope selector 10 via connectors (not shown). An endoscope 30 that conforms to the RGB sequential method is connected to the image-signal processing unit 40 and an endoscope 50 that conforms to the color chip method is connected to the image-signal processing unit 60. Each of the endoscopes 30 and 50 is detachably attached to respective image-signal processing units 40 and 60 by a scope connector (not shown). On the TV monitor 25, images captured by the endoscope 30 or 50 are alternatively displayed as an alternative selection by the electronic endoscope selector 10. The image displayed on the TV monitor 25 may be switched by operating switches on the control panel 22 (refer FIG. 2) of the electronic endoscope selector 10 or on the control panels 44 and 64 of the image-signal processing units 40 and 60. The images displayed on the TV monitor 25 may be simultaneously recorded on a videocassette tape by the VCR 26.

Firstly, a first electronic endoscope unit, to which the RGB sequential method is applied and is comprised of the endoscope 30 and the image-signal processing unit 40, is described as follows:

In the endoscope 30, the light guide 34, a bundle of extra fine optical fibers, is arranged. One end of the light guide 34 or emitting end 32 is arranged at the distal end of the endoscope 30. An illuminating lens (not shown) is provided in front of the emitting end 32. Light is emitted from the emitting end 32 and illuminates an object via the illuminating lens. This illumination light is supplied from the lamp (light source) 37, provided inside the image-signal processing unit 40, through the light guide 34.

Practically, parallel white light is emitted from the lamp 37 and concentrated on the incident end 35 of the light guide 34, via the condensing lens 36, and the RGB rotational filter 38. By this, light made incident to the incident end 35 is transmitted to the emitting end 32 through the light guide 34 and emitted from the distal end of the endoscope 30 to illuminate the interior of a cavity.

The RGB rotational filter 38 is a flat rotating disk, which has three openings formed at regular intervals in the rotating direction. On each opening, a red (R), green (G) and blue (B) colored filter is attached respectively. The RGB rotational filter 38 is revolved by the motor 39. The rotational axis of the filter 38 is in parallel with the optical axis of the illumination light emitted from the lamp 37. Further, the RGB rotational filter 38 is arranged so that each of the openings should traverse the light path of the illumination when the filter 38 is revolved. Namely, the white illumination light, which penetrates condensing lens 36, passes through each of the R, G, B filters when each opening traverses the light path, then it is concentrated on the incident end 35. The illumination light that penetrates the R, G and B filters becomes R, G, B light respectively, and each R, G, B light is sequentially made incident to the light guide 34 in regular intervals. Therefore, from the distal end of the endoscope 30, or the emitting end 32, the respective R, G and B light is emitted in regular intervals as illumination light.

The intensity of the lamp 37 is controlled by the lamp power circuit 46, which is controlled by the system control circuit 43. A control signal from the system control circuit 43 is a digital signal. The signal is converted to an analog signal by D/A converter 45 then fed to the lamp power circuit 46. The revolution of the motor 39 is controlled by a synchronized signal fed from the timing control circuit 42.

At the distal end of the endoscope 30, an imaging device 31, i.e., CCD, is provided. Image sensing is carried out by utilizing the R, G and B illumination, which is emitted from the emitting end 32. Since the illumination light is periodically emitted in the R, G and B color sequence, images corresponding to each R, G and B component are sensed by the imaging device 31 as sequential monochrome images. Captured images corresponding to each R, G and B component are transmitted as sequential RGB image signals, through the cable 33, to the image-signal processor 41, provided in the image-signal processing unit 40.

Image signals input to the image-signal processor 41 are subjected to prepositional signal processing, i.e., pre-amplifying and video bandwidth filtering, S/H (sample hold), amplifying, clamping, clipping, gamma correction, etc. The image signals are then converted to digital image signals. The digital image signals are temporally stored in the image memories (not shown) for each R, G, and B component as R, G, and B image data. When one set of image data comprising R, G and B images are prepared in the image memories, the R, G, B image data is converted to analog signals and postpositional signal processing is applied. In the postpositional signal processing, a filtering, amplifying, gamma correction, clamping, clipping, enhancing, signal level adjustment process and so on, are executed. The analog image signals are then transformed to the conventional standardized RGB component format, or in other words, RGB component video signals.

Note that, timing for driving the imaging device 31 and the image signal processing in the image-signal processor 41 are controlled by synchronized signals fed from the timing controller 42. The timing controller 42 is controlled by the system control circuit 43.

The control panel 44, with a switch group (not shown) mounted in the panel, is connected to the system control circuit 43. Further, the system control circuit 43 is connected with the system control circuit 21 (refer FIG. 2) of the electronic endoscope selector 10 via an interface cable Cl. When the control panel 44 is operated, the system control circuit 43 outputs a control signal by which the system control circuit 21, in the selector 10, switches the selection to the first electronic endoscope unit. Namely, when the first electronic endoscope unit is not selected by the electronic endoscope selector 10, and a switch on the control panel 44 is operated, the system control circuit 43 outputs a control signal to urge switching the selection, via the interface cable C1, to the system control circuit 21, and suspends the original function of the operated switch until the system control circuit 43 receives a response control signal from the system control circuit 21 via the interface cable C1, confirming the switch. The above operation for carrying out the selection at the electronic endoscope selector 10 can be achieved without providing a new switch to the control panel 44, and only modification to the control software may be required to apply the present embodiment to a conventional image-signal processing unit.

The RGB component video signals from the image-signal processor 41, and the synchronization signals from the timing control circuit 42, are fed to the electronic endoscope selector 10 via respective cables.

A second electronic endoscope unit, which the color chip method is applied and comprises the endoscope 50 and the image-signal processing unit 60, is described as follows:

The light guide 54, a bundle of extra fine optical fibers, is provided in the endoscope 50 and one end of the light guide 54, or emitting end 52, is arranged at the distal end of the endoscope 50. An illuminating lens (not shown) is provided in front of the emitting end 52 and light is emitted from the emitting end 52 and illuminates an object via the illuminating lens. This illumination light is supplied from the lamp (light source) 57, provided inside the image-signal processing unit 60, through the light guide 54. Practically, parallel white light is emitted from the lamp 57 and concentrated on the incident end 55 of the light guide 54 by the condensing lens 56. By this, light made incident to the incident end 55 is transmitted to the emitting end 52 through the light guide 54 and emitted from the distal end of the endoscope 50 as illumination.

Intensity of the lamp 57 is controlled by the lamp power circuit 66, which is in turn controlled by the system control circuit 63. A control signal from the system control circuit 63 is a digital signal. The signal is converted to an analog signal by D/A converter 65 then fed to the lamp power circuit 66.

At the distal end of the endoscope 50, an imaging device 51, such as a CCD with R, G, B color filters, is provided. At the imaging device 51, each R, G and B monochrome image is sensed simultaneously and fed to the image-signal processor 61 of the image-signal processing unit 60 via the cable 53 arranged inside the endoscope 50.

Image signals input to the image-signal processor 61 are subjected to prepositional signal processing, i.e., preamplifying and filtering of video bandwidth, S/H (sample hold), amplifying, clamping, clipping, gamma correction, etc. The image signals are then converted to digital image signals. The digital image signals are temporally stored in the image memories (not shown) for each R, G, and B component as R, G, and B image data. When one set of image data comprising R, G and B images are prepared in the image memories, the R, G, B image data is converted to analog signals and postpositional signal processing is applied. In the postpositional signal processing, filtering, amplifying, gamma correction, clamping, clipping, enhancing, signal level adjustment processes and so on, are executed. The analog image signals are then transformed to the conventional standardized RGB component format, in other words, RGB component video signals.

Note that, timing for driving the imaging device 51, and the image signal processing in the image-signal processor 61, is controlled by synchronized signals fed from the timing controller 62. The timing controller 62 is controlled by the system control circuit 63.

The control panel 64 with a switch group (not shown) mounted in the panel is connected to the system control circuit 63. Further, the system control circuit 63 is connected with the system control circuit 21 (refer FIG. 2), of the electronic endoscope selector 10, via an interface cable C2. When the control panel 64 is operated, the system control circuit 63 outputs a control signal, by which the system control circuit 21, in the selector 10, switches the selection to the second electronic endoscope unit. Namely, when the second electronic endoscope unit was not selected by the electronic endoscope selector 10, and a switch on the control panel 64 is operated, the system control circuit 63 outputs a control signal to urge switching the selection, via the interface cable C2 to the system control circuit 21, and suspends the original function of the operated switch until the system control circuit 63 receives a response control signal from the system control circuit 21 via the interface cable C2, confirming the switch.

The RGB component video signals from the image-signal processor 61 and the synchronization signals from the timing control circuit 62 are fed to the electronic endoscope selector 10 via respective cables.

Figure 2:
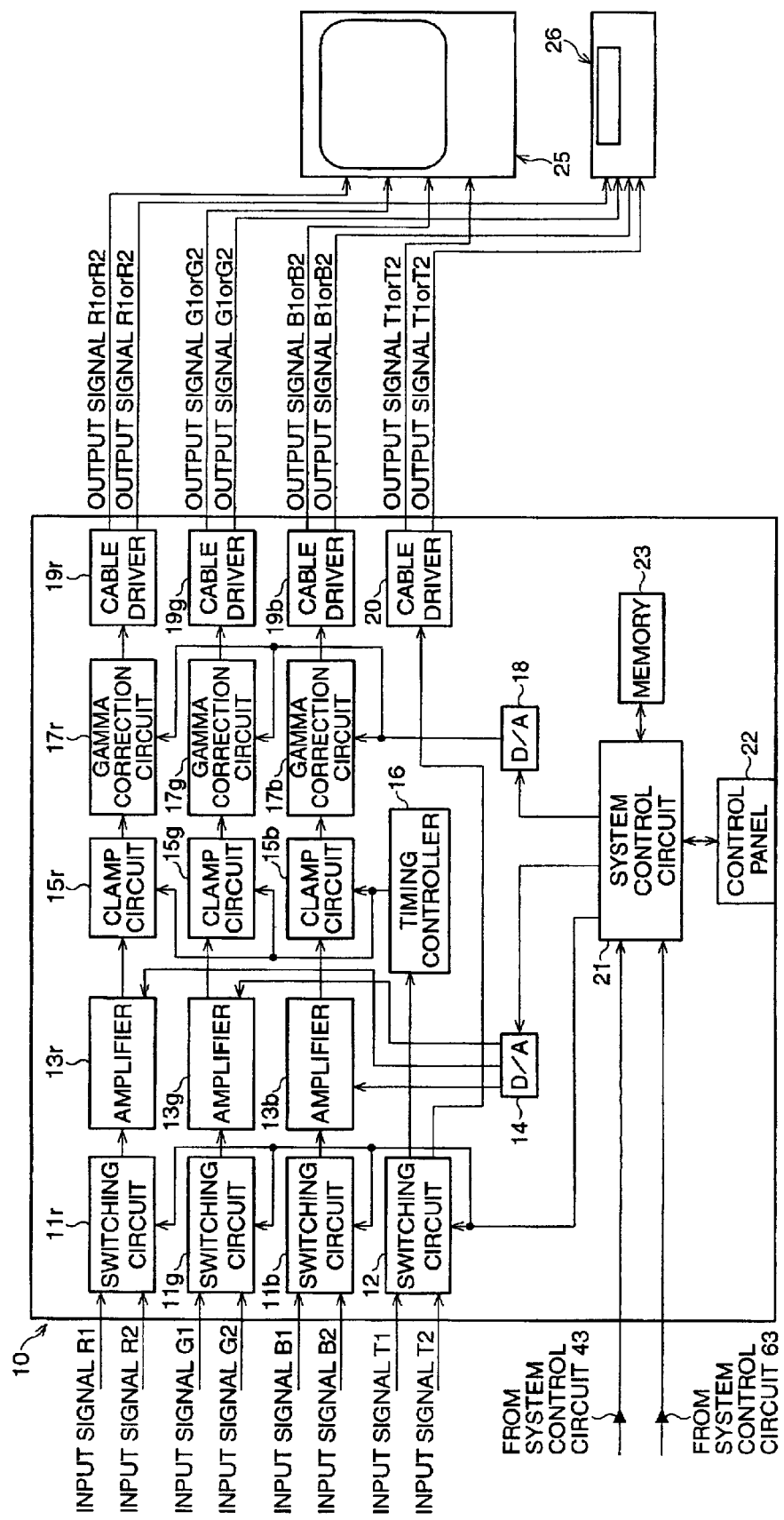
FIG. 2 is a schematic showing an electrical construction of an electronic endoscope selector of the present embodiment.

FIG. 2 is a schematic showing the electrical construction of the electronic endoscope selector 10 of the present embodiment. With reference to FIG. 2, the electronic endoscope selector 10 of the present embodiment is described.

As an example, switching circuits 11r, 11g, 11b and 12 are conventional analog and relay switches. The RGB component video signals R1, G1, B1 from the image-signal processing unit 40 and the RGB component video signals R2, G2, B2 from the image-signal processing unit 60 are input to the switching circuits 11r, 11g and 11b. The synchronization signals T1 and T2, which are fed from respective image-signal processing unit 40 and 60, are input to the switching circuit 12. At the switching circuits 11r, 11g, 11b and 12, either component signals (the RGB component video and synchronization signal) from the image-signal processing unit 40 or 60 are selected according to a control signal from the system control circuit 21, and output. Namely, when the first electronic endoscope unit is selected, the component signals (R1, G1, G1, T1) are output from the switching circuits 11r, 11g, 11b and 12. On the other hand, when the second electronic endoscope unit is selected, the component signals (R2, G2, G2, T2) are output from the switching circuits 11r, 11g, 11b and 12.

The RGB component video signals from the switching circuits 11r, 11g and 11b are amplified by amplifiers 13r, 13g and 13b, respectively, then output to respective clamp circuits 15r, 15g and 15b. At the clamp circuits 15r, 15g and 15b, the black level of the RGB component signals is adjusted and output to respective gamma correction circuits 17r, 17g and 17b. In each gamma correction circuit 17r, 17g and 17b, gamma correction for the RGB component video signals is executed, and the RGB component video signals are fed to the TV monitor 25 and VCR 26 via respective cable drivers 19r, 19g and 19b. On the other hand, the synchronization signal output from the switching circuit 12 is input to the timing controller 16 and a cable driver 20. The synchronization signal input to the cable driver 20 is fed to the TV monitor 25 and VCR 26.

The gains in the amplifiers 13r, 13g, 13b, for each of the RGB component video signals, are adjusted by a control signal from the system control circuit 21 through a D/A converter 14. Three channels are prepared for the D/A converter 14, and the control signal, which is a digital signal from the system control circuit 21, is converted to an analog signal at the D/A converter 14, then individually output to the respective amplifiers 13r, 13g, 13b. Namely, in each of the amplifiers 13r, 13g, 13b, the amount of gain is individually adjusted by the control signal from the system control circuit 21. The clamp circuits 15r, 15g and 15b are controlled by a synchronized signal from the timing controller 16. The gamma correction circuits 17r, 17g and 17b are controlled by control signals from the system control circuit 21, via a D/A converter 18.

A non-volatile memory 23 is also provided and connected to the system control circuit 21. The control signals output from the system control circuit 21 to the amplifiers 13r, 13g, 13b and gamma correction circuits 17r, 17g, 17b, provide a reference to the image-state parameters stored in the memory 23. The image-state parameters are sets of data corresponding to the RGB gain and gamma factors ($\gamma$). A set of image-state parameters for each electronic endoscope unit, which is connected to the electronic endoscope selector, are respectively stored in the memory 23. Namely, in the memory 23, two sets of image-state parameters for the respective video signals from the endoscope 30 and 50 are stored. The image-state parameters can be set or altered by operating switches on the control panel 22 connected to the system control circuit 21.

Figure 3:
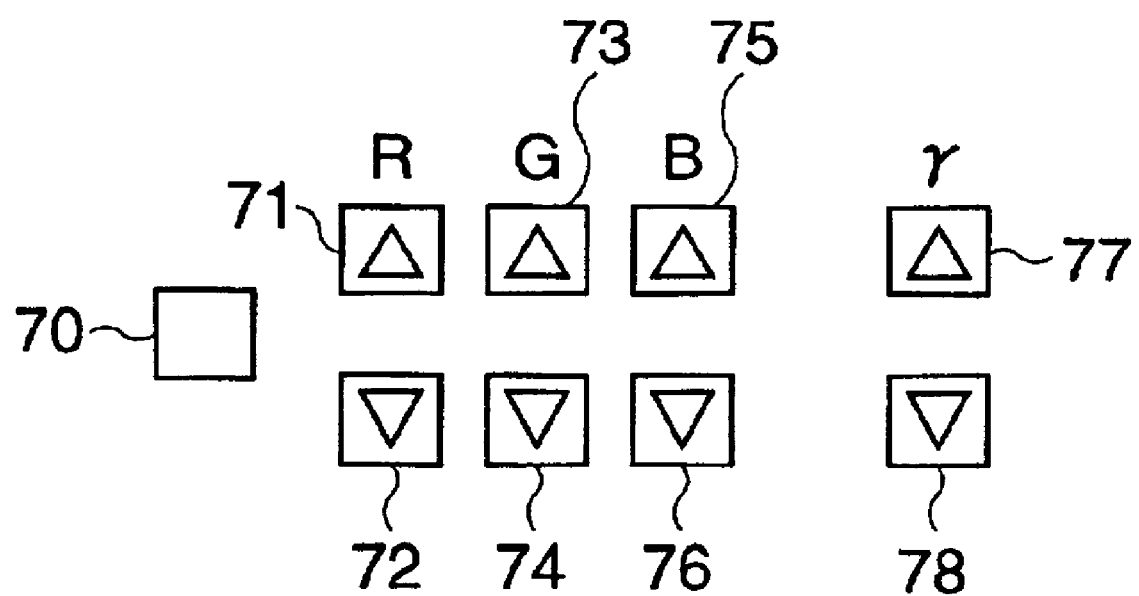
FIG. 3 illustrates an arrangement of switches on the control panel of the electronic endoscope selector for setting RGB gains and gamma factors.

FIG. 3 illustrates an arrangement of switches provided on the control panel 22, for setting the data of the image-state parameters, such as RGB gain and gamma factors.

A switch 70 is for an alternative selection of an electronic endoscope unit. When the switch 70 is pressed, output signals from each of the switching circuits 11r, 11g, 11b and 12 are alternately switched. Namely, when the component signals (R1, G1, B1, T1) are being output from each switching circuits 11r, 11g, 11b, 12 and the switch 70 is pressed, output signals is switched to the component signals (R2, G2, B2, T2). Contrarily, when the component signals (R2, G2, B2, T2) are being output from each switching circuits 11r, 11g, 11b, 12 and the switch 70 is pressed, output signals is switched to the component signals (R1, G1, B1, T1). At the same time, the image-state parameters, which are referenced to adjust the RGB gain and gamma correction, are also switched to parameters that correspond to the newly selected electronic endoscope unit, and the gains and gamma correction are adjusted according to the newly selected parameters.

Switches 71 through 76 individually vary and set the gains for respective R, G, B component video signal and adjust the color balance of the image. Each pair of switches 71, 72, switches 73, 74, and switches 75, 76 are for setting the respective R, G, B gain. The switches 71, 73 and 75 are for increasing the RGB gain and switches 72, 74 and 76 are for decreasing the RGB gain. The gamma factor ($\gamma$) for the gamma correction is varied and set by the switches 77 and 78. When the switch 77 is pressed, the gamma factor is increased. Contrarily, when the switch 78 is pressed, the gamma factor is decreased. When one of the above switches is operated, the image-state parameters for the current electronic endoscope unit are renewed immediately. In other words, the data renewal of the image-state parameters in the memory 23, is phased in accordance with the number or length of time the above switches are pressed. For example, when the first electronic endoscope unit is selected and one of the switches 71–78 is pressed, the image-state parameters (the RGB gain data or $\gamma$ data) stored in the memory 23, for the first electronic endoscope unit, is rewritten by the system control circuit 21. The system control unit 21 controls the amplifiers 13r, 13g, 13b and gamma correction circuits 17r, 17g, 17b in accordance with the rewritten image-state parameters stored in the memory 23. The RGB gain and gamma correction for the RGB component video signals (R1, G1, B1), from the first electronic endoscope unit, are adjusted to the renewed image-state parameters in each of the amplifiers 13r, 13g, 13b and gamma correction circuits 17r, 17g, 17b and fed to the TV monitor 25 and VCR 26.

Note that adjustments for the RGB gain (color balance) and gamma factor are primarily set by taking the image of a white chart, for example, and adjusting the image of the white chart on the TV monitor 25 to become the same for each electronic endoscope unit by operating the switches 71–78.

As described above, according to the present embodiment, since the electronic endoscope selector stores the RGB gain and gamma factors corresponding to each of the electronic endoscope units, and image signal processing can be executed in accordance with the above stored image-state parameters, the color tone of the displayed image for each electronic endoscope unit is easily adjusted by the operation on the electronic endoscope selector only. Further, image signal processing for the color tone adjustment at the electronic endoscope selector, is automatically executed in accordance with the image-state parameters that correspond to the selected electronic endoscope unit. Therefore, the necessity for an operator to select new image-state parameters that correspond to a newly selected electronic endoscope unit at each switching operation is eliminated, and consequently, the operational faculty is improved.

Note that, in the present embodiment, there are only two electronic endoscope units connected to the electronic endoscope selector, the number of electronic endoscope units may be increased.

In the present embodiment, although the color balance is controlled by adjustment for the respective gain of R, G and B component, it may be controlled by adjusting relative gains of the R and B component to the G component, for example.

Although the embodiments of the present invention have been described herein with reference to the accompanying drawings, obviously many modifications and changes may be made by those skilled in this art without departing from the scope of the invention.

The present disclosure relates to subject matter contained in Japanese Patent Application No. 2000-002641 (filed on Jan. 11, 2000), which is expressly incorporated herein, by reference, in their entireties.

What is claimed is:

1. An electronic endoscope selector comprising:
    a video signal switching processor that selects one electronic endoscope unit among a plurality of electronic endoscope units and feeds video signals obtained by the selected electronic endoscope unit to an image indicating device, said selected electronic endoscope unit being switchable to another;
    a video-signal processor that processes said video signals, which are fed to said image indicating device, to adjust a color tone of an image displayed on said image indicating device;
    an image-state parameter storing processor that stores image-state parameters by which said color tone is adjusted and which correspond to each of said plurality of electronic endoscope units; and
    an image-state parameter setting processor that is used to set said image-state parameters.

2. A selector according to claim 1, wherein said video-signal processor adjusts said color tone by adjusting gains and gamma factors of said video signals and said image-state parameters correspond to said gains and gamma factors.

3. A selector according to claim 2, wherein said video signals comprise red, green and blue component video signals and said gains are adjusted relative to each said red, green and blue video signals.

4. A selector according to claim 1, wherein said video-signal processor starts to process video signals fed from an electronic endoscope unit, that is newly selected by said video signal switching processor, in accordance with said image-state parameters which correspond to the newly selected electronic endoscope unit, when a selected electronic endoscope unit is switched to said newly selected electronic endoscope unit.

5. An electronic endoscope system comprising:
   a plurality of electronic endoscope units;
   an image indicating device;
   an electronic endoscope selector; and
   wherein said electronic endoscope selector comprises:
   a video signal switching processor that selects one electronic endoscope unit among said plurality of electronic endoscope units and feeds video signals obtained by the selected electronic endoscope unit to said image indicating device, said selected electronic endoscope unit being switchable to another;
   a video-signal processor that processes said video signals fed to said image indicating device, to adjust a color tone of an image displayed on said image indicating device;
   an image-state parameter storing processor that stores image-state parameters which correspond to each of said plurality of electronic endoscope units and by which said color tone is adjusted; and
   an image-state parameter setting processor that is used to set said image-state parameters.

* * * * *